(12) United States Patent
Herbst et al.

(10) Patent No.: US 7,053,261 B2
(45) Date of Patent: May 30, 2006

(54) PROCESS FOR PARAFFIN HYDROCARBON ISOMERIZATION AND COMPOSITE CATALYST THEREFORE

(75) Inventors: Konrad Herbst, Lyngby (DK); Jindrich Houzvicka, Holte (DK); Birgitte Tofte Jespersen, Roskilde (DK); John Zavilla, Kokkedal (DK)

(73) Assignee: Haldor Topsoe A/S, Lyngby (DK)

( * ) Notice: Subject to any disclaimer, the term of this patent is extended or adjusted under 35 U.S.C. 154(b) by 522 days.

(21) Appl. No.: 10/387,545

(22) Filed: Mar. 14, 2003

(65) Prior Publication Data

US 2003/0181780 A1    Sep. 25, 2003

(30) Foreign Application Priority Data

Mar. 22, 2002    (DK) .................... PA 2002 00439

(51) Int. Cl.
    *C07C 5/22*    (2006.01)
(52) U.S. Cl. ........................ 585/747; 585/734
(58) Field of Classification Search ........... 585/747, 585/734
    See application file for complete search history.

(56) References Cited

U.S. PATENT DOCUMENTS

| 5,104,840 A | 4/1992 | Chauvin et al. |
| 5,202,519 A | 4/1993 | Khare |
| 5,358,919 A | 10/1994 | Wu |
| 5,874,638 A | 2/1999 | Chauvin et al. |
| 2002/0010291 A1 | 1/2002 | Murphy |

FOREIGN PATENT DOCUMENTS

| EP | 1177199 B1 | 4/2000 |
| EP | 1182197 A1 | 8/2000 |
| EP | 1 035 093 A | 9/2000 |
| EP | 1120159 A1 | 8/2001 |
| EP | 1 310 472 A | 5/2003 |
| WO | WO-95/21872 | 8/1995 |
| WO | WO-96/18459 A1 | 6/1996 |

OTHER PUBLICATIONS

"Ionic Liquids—New "Solutions" for Transition Metal Catalysis" by Peter Wasserscheid* and Wilhelm Keim, pp. 3772-3789.

"Catalytic reactions in ionic liquids" by Roger Sheldon, Chem. Commun., 2001, pp. 2399-2407.

"Room-Temperature Ionic Liquids. Solvents for Synthesis and Catalysis" by Thomas Welton, Chem. Rev. 1999, 99, pp. 2071-2083.

*Primary Examiner*—Thuan D Dang
(74) *Attorney, Agent, or Firm*—Dickstein Shapiro Morin & Oshinsky LLP

(57) ABSTRACT

A process for the conversion of linear and/or branched paraffin hydrocarbons based on the use of an ionic liquid catalyst in combination with a metal salt additive, which provides a catalytic composition with an increased activity, compared with said ionic liquid. Under suitable reaction conditions this conversion is leading to paraffin hydrocarbon fraction with higher octane number.

11 Claims, No Drawings

PROCESS FOR PARAFFIN HYDROCARBON ISOMERIZATION AND COMPOSITE CATALYST THEREFORE

BACKGROUND OF THE INVENTION AND PRIOR ART

The present invention relates to a process for the isomerization of paraffin hydrocarbons catalysed by a mixture of an acidic ionic liquid catalyst and a metal salt.

Paraffin hydrocarbons with high degree of branching are known to be useful blending components for motor gasoline due to their high octane numbers. Such paraffin hydrocarbon fractions can be produced in an isomerization process increasing the octane number of the $C_4$–$C_9$ cuts. Isomerization of $C_4$, $C_5$ and $C_6$ paraffins are common refinery processes based on use of a Friedel-Crafts catalyst such as $AlCl_3$ or a group 8–10 metal (using current IUPAC nomenclature for the Periodic Table of elements with groups from 1–18) supported on a halogenated, preferably chlorinated, carrier. Processes including higher fractions ($C_7$ to $C_9$ hydrocarbons) meet with significant difficulties due to low selectivity and low octane number of the once-through products.

The use of combinations of aluminium halides (in particular $AlCl_3$) and certain anhydrous metal chlorides or sulphates (in particular $CuCl_2$ or $CuSO_4$) for alkane isomerization is known and has been described in several scientific articles. Ono et al. (Chem. Lett. (1978), 1061; Chem. Lett. (1978), 625; J. Catal. 56 (1979) 47; J. Catal. 64 (1980) 13) describes pentane isomerization at room temperature to 323 K by a series of physical mixtures of $AlCl_3$ or $AlBr_3$ with approximately 30 different metal salts. The highest conversions were obtained for mixtures of $AlCl_3$ with anhydrous copper (II) salts preferentially $CuCl_2$ and $CuSO_4$. It was noticed that maximum conversions occurred at defined was noticed that maximum conversions occurred at defined $AlCl_3/CuCl_2$ or $AlCl_3/CuSO_4$ molar ratios of 0.5. This suggested that a specific compound was formed as active species with super-acid property. This conclusion was supported by acidity measurements showing that the acid strength of the $AlCl_3/CuSO_4$ mixture was found to be relatively higher than that of $AlCl_3$ alone. By independent synthesis (N. Kitayima, Y. Ono, J. Mol. Catal. 10 (1981) 121) the mixed metal chloride $Cu(AlCl_4)_2$ was obtained with 20 times higher isomerization activity at room temperature than physical mixtures of $AlCl_3$ and $CuCl_2$.

Another example on the use of combinations of $AlCl_3$ based isomerization systems with metal salt additives is described in U.S. Pat. No. 5,202,519, which discloses mixtures of an aluminium halide (preferably $AlCl_3$), calcium aluminate, a copper (II) salt (preferably $CuCl_2$) and an alcohol. The molar ratio of aluminium halide:Cu salt was preferably 3:1 to 2:1. This mixture was shaped and the shaped particles were dried. This catalyst composition was used in the isomerization of $C_4$–$C_{10}$ alkanes and/or $C_5$–$C_{10}$ cycloalkanes at temperatures of up to 300° C., more preferentially at temperatures of 20–40° C. In the isomerization of n-pentane at 24° C., a conversion of 95.5% was obtained, however, the selectivity to isomerization products was lower than the selectivity to disproportionation and cracking products ($C_4$, $C_{6+}$). In the isomerization of methyl-heptane this catalyst composition showed a much lower conversion of 54.6% again with a low selectivity to isomerization products due to substantial conversion of the feed to higher and lower isoalkanes.

While known art using combinations of aluminium halides with (transition) metals concentrates on copper salts as most effective additives, the choice of additive is not restricted exclusively to this metal. In U.S. Pat. No. 5,358,919 alumina is impregnated with a sulphate solution of copper, iron, cobalt, nickel, manganese, zinc or magnesium. After a calcination step the obtained material was mixed with $AlCl_3$ and a chlorinated hydrocarbon and this mixture heated to 40–90° C. This composite catalyst was used in isomerization reactions of alkanes and cycloalkanes preferably at temperatures of 20–50° C.

A different example on the use of metal salts as additives to a catalyst for paraffin isomerization is described in the article J. Chem. Soc., Perkin Trans 2, 1999, pages 2715–2718. In this case the hexane isomerization catalysed by a liquid superacid, trifluoromethanesulphonic acid ($CF_3SO_3H$) is investigated in the presence of $FeCl_3$ and $CuCl_2$. The experiments were carried out as batch reactions in a capped tube (containing hexane and $CF_3SO_3H$) without stirring in order to have a well defined contact area throughout the study of the isomerization kinetics. Adding a small amount (not specified) of $FeCl_3$ and $CuCl_2$, respectively, resulted in the activation of the system and a relative faster conversion of hexane to isomeric product was observed.

A relatively new class of acidic catalysts based on ionic liquids has been described in the literature (P. Wasserscheid, W. Keim, Angew. Chem., Int. Ed., 2000, V. 39, pages 3772–3789; T. Welton, Chem. Rev., 1999, V. 99, pages 2071–2083). This group of compounds also referred to as molten salts are constituted of:

(1) an inorganic anion, typically formed from metal halides, such as $AlCl_4^-$, $Al_2Cl_7^-$, or other inorganic anions ($SO_4^{2-}$, $NO_3^-$, $PF_6^-$, $CF_3SO_3^-$, $BF_4^-$ etc.), and
(2) an organic cation, typically derived from N-heterocyclic or alkylammonium entities.

The melting point of ionic liquids is relatively low and an increasing number of ionic liquids are described with melting points below room temperature. Below some characteristics of ionic liquids are listed:

(1) They have a liquid range of about 300° C.
(2) They are good solvents for a wide range of inorganic, organic and polymeric materials.
(3) They exhibit Broensted and Lewis acidity as well as superacidity.
(4) They have low or no vapour pressure.
(5) Most ionic liquids are thermally stable up to near 200° C., some ionic liquids are stable at much higher temperature (about 400–450° C.).
(6) They are relatively cheap and easy to prepare and upscale.
(7) They are non-flammable and easy in operation.
(8) They are highly polar but non-coordinating materials.

Ionic liquids most frequently demonstrate Lewis acidic properties once they are formed by metal halides. In many cases, however, the ionic liquids also show strong Broensted (proton) acidity. The proton acidity may originate both from the cation if it contains a proton at the quarternized N atom, or from the anion if it contains protons, for instance in $HSO_4^-$, $H_2PO_4^-$.

Also HCl produced via partial hydrolysis for example of the chloroaluminate anion can explain strong proton acidity of the ionic liquids.

Lewis-acidic properties of ionic liquids are governed by two major factors: (1) the nature of the anion, and (2) the molar ratio of the organic part to the inorganic part (for instance, in the case of ionic liquids based on metal halides $Me(Hal)_n$ by the molar fraction of $Me(Hal)_n$). If $X_{Me(Hal)n} < 0.5$, the ionic liquid is called basic; if $X_{Me(Hal)n} = 0.5$, this is the case of neutral ionic liquid, and finally if $X_{Me(Hal)_n}$ >0.5, the ionic liquid can be classified as acidic or in some cases superacidic.

The effect of superacidity of ionic liquids is quite frequently observed for $AlCl_3$-based compositions. Sometimes this effect is related to the presence of dry HCl in the system, which is dissolved in the ionic liquid. The Hammett function $H_0$ for such systems ($H_0$=−18) indicates superacidic properties of the ionic liquids comparable with those of HF—$TaF_5$ ($H_0$=−16) and "magic acid" HF—$SbF_5$ or $FSO_3H$—$SbF_5$ ($H_0$=−25). All these systems are much stronger acids as compared to the conventional 100% $H_2SO_4$ ($H_0$=−12), which marks the border of superacidity. Such ionic liquids are also stronger than the solid superacids like $SO_4/ZrO_2$ ($H_0$=−16), $H_3PW_{12}O_{40}$ ($H_0$=−13.5) or H-Nafion ($H_0$=−12).

Room-temperature ionic liquids are promising media for a wide range of catalytic reactions including downstream oil processing, basic organic synthesis and fine chemicals production. Among these processes of potential commercial interest are various alkylation, oligomerisation and isomerization reactions.

DETAILED DESCRIPTION OF THE INVENTION

The object of the present invention is a process for the conversion of linear and/or branched paraffin hydrocarbons in presence of an ionic liquid catalyst combined with a metal salt additive, which provides a catalytic composition with improved activity compared to ionic liquid. Under appropriate reaction conditions this conversion is leading to paraffin hydrocarbon fraction with higher octane number.

The invention therefore concerns a process for isomerization of paraffin hydrocarbon feed in the presence of a composite catalyst containing
(a) an ionic liquid catalyst comprised of a N-containing heterocyclic and/or aliphatic organic cation and an inorganic anion derived from metal halides or mixed metal halides, and
(b) a metal salt additive comprising
  (i) at least one metal salt containing a cation chosen from group 6, 8, 11 or 12.
  (ii) a mixed metal compound containing at least one cation chosen from group 6, 8, 11 or 12.
  (iii) an inorganic or organometallic co-ordination compound containing at least one metal chosen from group 6, 8, 11 or 12 as cationic, neutral or anionic complex.

The invention also concerns a composite catalyst for use in the above process.

The ionic liquids used for the hydrocarbon isomerization reaction represent salts formed by an organic cation such as N-containing heterocyclic or N-containing aliphatic moiety and an inorganic anion, which may be an anion derived from metal halides or mixed metal halides. The cation may be an alkyl substituted pyridinium, piperidinium, quinolinium (or similar amine compounds) with one or several alkyl or aryl groups or an alkyl ammonium (mono-, di-, tri- or tetra-alkyl ammonium compound). The anion may be derived from any metal halide or mixed metal halide with strong Lewis acidic properties, for instance $AlCl_4^-$, $AlBr_4^-$, $GaCl_4^-$, $Al_2Cl_7^-$, $Al_2Cl_6Br^-$ and the like. The ionic liquid chosen for paraffin isomerization may be characterised by the amine: Lewis acid molar ratio from 1:3 to 2:1, more preferably from 1:2.5 to 1:1.

The metal salt additives used in combination with the ionic liquids as catalysts can be chosen from anhydrous compounds containing a metal cation chosen from group 6, 8, 11 or 12 (Periodic Table, New notation) and an anion such as a halogenide, hydroxy-halogenide or sulphate. Physical mixtures of several of these anhydrous compounds also may be used. The additive also may be chosen from mixed-metal compounds like $Cu(AlCl_4)_2$ or inorganic coordination compounds containing a group 6, 8, 11 or 12 metal as part of the cationic, neutral or anionic component of the coordination compound like e.g. $[NMe_3H]_2[CuCl_4]$. Preferably, the additives are chosen from compounds containing molybdenum (V), iron (III) or copper (II). The molar ratio between the metal in the ionic liquid and metal salt additive can be varied above 1:1, more preferably above 2:1.

The metal salt additive can be added in solid anhydrous form to the ionic liquid, wherein the metal salt additive is completely or partially soluble. It may also be added in liquid form since e.g. $CuCl_2$ and $FeCl_3$, respectively, form liquids with some N-containing heterocyclic and/or aliphatic moieties (e.g. trimethylammonium heptachlorodiferrate). In order to form a saturated solution of the metal salt additive in the ionic liquid the mixture is treated by an appropriate means, which might comprise e.g. heat treatment or ultrasound treatment for several hours. In case of a partial solubility of the metal salt additive in the ionic liquid a slurry phase is obtained containing finely divided powder of said metal salt additive. This mixture may be used as prepared in isomerization reactions or may be filtered under inert conditions over an appropriate filter agent to remove the solid before contacting the catalyst with the hydrocarbon feed.

The solubility of hydrocarbons in ionic liquids is limited and for instance paraffins and naphthenes are generally immiscible with ionic liquids. Olefins and aromatic compounds demonstrate a clear dependence of the solubility on the oleophilic properties of the ionic liquid. The longer the chain length of the radical attached to the N-heterocyclic moiety, the higher the solubility of olefins and aromatics in the ionic liquids. However, most of the commonly used organic solvents and reagents are immiscible with ionic liquids. This simplifies the use of ionic liquids in a biphasic system and provides a procedure for a simple product/catalyst separation.

Paraffin isomerization can be carried out in pressurised equipment under high pressure or in a glass vessel at atmospheric pressure. The pressure in the autoclave can be varied from 1 bar to 60 bar. Any gas like helium, argon, nitrogen, hydrogen or dry air can be used in the reaction. The reaction temperature can vary in a range from −30° C. to 150° C. Temperatures out of this range can also be used, although they are less preferred.

Linear n-paraffins such as n-butane, n-pentane, n-hexane, n-heptane, n-octane, n-nonane and monomethylalkanes, such as 2- and 3-methylhexane or a mixture thereof can be used as substrates of the isomerization process, forming a product containing paraffin hydrocarbons with a higher degree of branching.

The hydrocarbon feed used for the isomerization experiments is a mixture of the following compounds: 19 wt % n-heptane, 21 wt % 2-methylhexane, 21 wt % 3-methylhexane, 36 wt % methylcyclohexane, 1 wt % 2,4-dimethylpentane, 1,7 wt % 2,3 dimethylpentane and 0,3 wt % of other $C_7$ isomer compounds.

EXAMPLES

Example 1

In an inert atmosphere ($N_2$) trimethylamine hydrochloride (39.13 g, 0.409 mole) is added to aluminium chloride (98.28 g, 0.737 mole). The light-brown viscous melt which forms is heated to 90° C. under stirring and kept at this temperature for 2 h. From the resulting liquid may precipitate some solid $AlCl_3$ after cooling to room temperature assuring that a maximum amount of $AlCl_3$ is dissolved. In the isomerization experiments described below only the liquid phase has been used as catalyst. The ionic liquid can be stored in inert atmosphere ($N_2$) without decomposition.

Example 2

In an inert atmosphere ($N_2$) a 2-neck Schlenk flask equipped with a mechanical stirrer is charged with 30 ml ionic liquid (42 g) prepared according to Example 1. A specified amount of anhydrous metal salt (see Tables 1 and 2) previously dried by an appropriate drying agent or by heat treatment is added to the ionic liquid. The mixture is heated under vigorous stirring (700 rpm) to 90° C. for 1 h in order to get a saturated solution of the additive in the ionic liquid. However, with the chosen amounts of metal salt additive, a part of the additive remains undissolved as a solid forming a slurry. After heating the mixture is cooled to room temperature in an inert atmosphere ($N_2$).

Example 3

In an inert atmosphere ($N_2$) a 2-neck Schlenk flask fitted with a mechanical stirrer is charged with 30 ml ionic liquid (42 g) prepared according to Example 1. Anhydrous $CuCl_2$ (1.73 g), previously dried by heat treatment, is added to the ionic liquid. The mixture is treated under vigorous stirring (700 rpm) by ultrasound for 1 h thereby forming a slurry phase with the ionic liquid, which contains partially dissolved additive.

Examples 4–30

In an inert atmosphere ($N_2$) in a 2-neck Schlenk flask equipped with mechanical stirring, 30 ml paraffin feed is added to 30 ml of the ionic liquid catalyst prepared according to Examples 1–3. The two-phase system is vigorously stirred (700 rpm) at a constant temperature chosen between 0 and 50° C. Samples of the paraffin phase are taken after 5 min, 10 min, 15 min, 30 min and 60 min and analysed by a gas chromatograph.

Tables 1 and 2

Definitions:

Multi-branched $C_7$ products: Dimethylpentanes and trimethyl-butane.

$C_{6-}$ products: Compounds containing six and less than six carbon atoms.

$C_{8+}$ products: Compounds containing eight and more than eight carbon atoms.

Normalised yield of multi-branched $C_7$ products is defined as:

100×(sum of multi-branched $C_7$ products)/(sum of $C_7$ compounds excluding cyclic $C_7$ compounds)

Selectivity to multibranched $C_7$ products is defined as:

100×(sum of multi-branched $C_7$ products)/(sum of multi-branched $C_7$ products+$C_{6-}$ products+$C_{8+}$ products).

TABLE 1

| Example | Additive | Amount of additive (g) | Temperature (° C.) | Time (min) | Normalised yield of multi-branched $C_7$ products (wt %) | Selectivity to multi-branched $C_7$ products (wt %) |
|---|---|---|---|---|---|---|
| 4 | No additive (Reference Example) | | 25 | 5 | 4.7 | 97.7 |
| | | | | 10 | 5.0 | 97.8 |
| | | | | 15 | 5.2 | 97.9 |
| | | | | 30 | 5.9 | 98.2 |
| | | | | 60 | 6.7 | 96.2 |
| 5 | $MoCl_5$ | 3.52 | 25 | 5 | 15.3 | 97.6 |
| | | | | 10 | 19.0 | 97.1 |
| | | | | 15 | 20.9 | 97.3 |
| | | | | 30 | 23.8 | 96.2 |
| | | | | 60 | 26.3 | 94.5 |
| 6 | $FeCl_3$ | 2.08 | 25 | 5 | 10.5 | 96.9 |
| | | | | 10 | 15.8 | 97.6 |
| | | | | 15 | 19.9 | 96.6 |
| | | | | 30 | 24.4 | 95.2 |
| | | | | 60 | 27.7 | 92.7 |
| 7 | $FeCl_3$ | 2.08 | 50 | 5 | 14.6 | 95.5 |
| | | | | 10 | 17.0 | 95.4 |
| | | | | 15 | 18.8 | 94.7 |
| | | | | 30 | 21.8 | 92.4 |
| | | | | 60 | 25.0 | 88.5 |
| 8 | $CuCl_2$ | 1.82 | 0 | 5 | 4.9 | 97.4 |
| | | | | 10 | 7.5 | 99.3 |
| | | | | 15 | 11.7 | 98.9 |
| | | | | 30 | 19.4 | 95.5 |
| | | | | 60 | 27.6 | 97.5 |
| 9 | $CuCl_2$ | 1.82 | 25 | 5 | 8.0 | 96.3 |
| | | | | 10 | 25.1 | 89.7 |
| | | | | 15 | 28.6 | 81.4 |

TABLE 1-continued

| Example | Additive | Amount of additive (g) | Temperature (° C.) | Time (min) | Normalised yield of multi-branched C$_7$ products (wt %) | Selectivity to multi-branched C$_7$ products (wt %) |
|---|---|---|---|---|---|---|
|  |  |  |  | 30 | 30.3 | 79.3 |
|  |  |  |  | 60 | 30.3 | 71.5 |
| 10 | CuCl$_2$ | 1.82 | 50 | 15 | 29.2 | 72.6 |
|  |  |  |  | 30 | 29.7 | 71.6 |
|  |  |  |  | 60 | 30.5 | 68.7 |
| 11 | CuCl$_2$ Treated by ultra-sound (Example 3) | 1.73 | 25 | 5 | 7.7 | 98.1 |
|  |  |  |  | 10 | 20.4 | 94.8 |
|  |  |  |  | 15 | 28.0 | 85.9 |
|  |  |  |  | 30 | 30.6 | 78.0 |
|  |  |  |  | 60 | 32.1 | 72.8 |
| 12 | CuCl$_2$ | 4.04 | 25 | 5 | 6.4 | 98.1 |
|  |  |  |  | 10 | 15.8 | 97.4 |
|  |  |  |  | 15 | 25.1 | 85.5 |
|  |  |  |  | 30 | 30.1 | 75.3 |
|  |  |  |  | 60 | 31.1 | 72.6 |
| 13 | CuCl$_2$ + FeCl$_3$ | 0.87 g CuCl$_2$ + 1.04 g FeCl$_3$ | 25 | 5 | 10.0 | 98.5 |
|  |  |  |  | 10 | 23.3 | 92.3 |
|  |  |  |  | 15 | 25.7 | 89.4 |
|  |  |  |  | 30 | 28.4 | 86.3 |
|  |  |  |  | 60 | 29.5 | 84.2 |
| 14 | Cu(AlCl$_4$)$_2$ | 1.60 | 25 | 5 | 27.6 | 98.3 |
|  |  |  |  | 10 | 29.3 | 96.2 |
|  |  |  |  | 15 | 30.1 | 93.6 |
|  |  |  |  | 30 | 30.9 | 87.9 |
|  |  |  |  | 60 | 31.8 | 79.3 |
| 15 | [NMe$_3$H]$_2$[CuCl$_4$] | 2.10 | 25 | 5 | 8.4 | 97.2 |
|  |  |  |  | 10 | 15.6 | 91.4 |
|  |  |  |  | 15 | 17.1 | 90.4 |
|  |  |  |  | 30 | 18.2 | 90.8 |
|  |  |  |  | 60 | 19.4 | 90.5 |
| 16 | CuCl$_2$, filtered | 1.82 | 25 | 5 | 8.2 | 92.7 |
|  |  |  |  | 10 | 13.8 | 94.3 |
|  |  |  |  | 15 | 15.2 | 94.5 |
|  |  |  |  | 30 | 16.8 | 94.6 |
|  |  |  |  | 60 | 18.3 | 94.5 |
| 17 | CuCl$_2$ (Catalyst: feed volume ratio 1:4) | 1.74 | 25 | 10 | 9.5 | 89.3 |
|  |  |  |  | 15 | 12.6 | 96.1 |
|  |  |  |  | 30 | 15.4 | 95.2 |
|  |  |  |  | 60 | 16.7 | 95.6 |
| 18 | CuCl$_2$ (Catalyst: feed volume ratio 2:1) | 1.73 | 25 | 5 | 27.7 | 85.5 |
|  |  |  |  | 10 | 29.8 | 75.7 |
|  |  |  |  | 15 | 30.7 | 74.8 |
|  |  |  |  | 30 | 31.8 | 70.8 |
|  |  |  |  | 60 | 32.7 | 67.8 |
| 19 | CuSO$_4$ | 2.05 | 25 | 5 | 7.8 | 97.7 |
|  |  |  |  | 10 | 22.5 | 89.5 |
|  |  |  |  | 15 | 26.5 | 76.3 |
|  |  |  |  | 30 | 28.2 | 77.1 |
|  |  |  |  | 60 | 29.4 | 68.5 |
| 20 | Cu(OH)Cl | 1.27 | 25 | 5 | 9.6 | 95.9 |
|  |  |  |  | 10 | 13.6 | 94.0 |
|  |  |  |  | 15 | 14.8 | 93.9 |
|  |  |  |  | 30 | 16.8 | 93.5 |
|  |  |  |  | 60 | 19.6 | 93.2 |
| 21 | CuI | 2.45 | 25 | 5 | 4.7 | 97.1 |
|  |  |  |  | 10 | 5.0 | 97.4 |
|  |  |  |  | 15 | 5.5 | 97.7 |
|  |  |  |  | 30 | 6.6 | 98.1 |
|  |  |  |  | 60 | 8.4 | 98.6 |
| 22 | ZnCl$_2$ | 1.75 | 25 | 5 | 4.8 | 95.1 |
|  |  |  |  | 10 | 5.2 | 95.8 |
|  |  |  |  | 15 | 5.7 | 96.1 |
|  |  |  |  | 30 | 6.6 | 96.9 |
|  |  |  |  | 60 | 8.3 | 96.5 |

TABLE 2

Comparative Examples

| Example | Additive | Amount of additive (g) | Temperature (° C.) | Time (min) | Normalised yield of multi-branched $C_7$ products (wt %) | Selectivity to multi-branched $C_7$ products (wt %) |
|---|---|---|---|---|---|---|
| 23 | $ZrCl_4$ | 3.00 | 25 | 5 | 4.7 | 97.1 |
|  |  |  |  | 10 | 5.1 | 97.4 |
|  |  |  |  | 15 | 5.4 | 97.8 |
|  |  |  |  | 30 | 6.2 | 98.3 |
|  |  |  |  | 60 | 7.5 | 98.0 |
| 24 | $AlCl_3$ | 1.72 | 25 | 5 | 4.7 | 97.4 |
|  |  |  |  | 10 | 5.1 | 97.7 |
|  |  |  |  | 15 | 5.6 | 97.7 |
|  |  |  |  | 30 | 6.9 | 98.3 |
|  |  |  |  | 60 | 8.6 | 88.5 |
| 25 | $AlCl_3$ | 5.19 | 25 | 5 | 5.2 | 95.3 |
|  |  |  |  | 10 | 6.2 | 91.0 |
|  |  |  |  | 15 | 6.9 | 88.7 |
|  |  |  |  | 30 | 7.9 | 90.1 |
|  |  |  |  | 60 | 9.0 | 93.7 |
| 26 | $TiCl_3$ | 1.79 | 25 | 5 | 4.4 | 96.2 |
|  |  |  |  | 10 | 4.5 | 96.2 |
|  |  |  |  | 15 | 4.6 | 96.0 |
|  |  |  |  | 30 | 4.8 | 97.1 |
|  |  |  |  | 60 | 5.1 | 94.2 |
| 27 | $NbCl_5$ | 3.48 | 25 | 5 | 4.5 | 97.1 |
|  |  |  |  | 10 | 4.7 | 96.9 |
|  |  |  |  | 15 | 4.9 | 97.1 |
|  |  |  |  | 30 | 5.3 | 97.3 |
|  |  |  |  | 60 | 5.9 | 97.7 |
| 28 | $MnCl_2$ | 1.62 | 25 | 5 | 4.6 | 97.5 |
|  |  |  |  | 10 | 4.7 | 97.6 |
|  |  |  |  | 15 | 4.7 | 95.3 |
|  |  |  |  | 30 | 4.8 | 96.4 |
|  |  |  |  | 60 | 4.9 | 97.2 |
| 29 | $CoCl_2$ | 1.67 | 25 | 5 | 4.7 | 98.1 |
|  |  |  |  | 10 | 4.8 | 97.9 |
|  |  |  |  | 15 | 4.9 | 97.9 |
|  |  |  |  | 30 | 5.2 | 97.2 |
|  |  |  |  | 60 | 5.5 | 98.0 |
| 30 | $NiCl_2$ | 1.67 | 25 | 5 | 4.4 | 96.2 |
|  |  |  |  | 10 | 4.5 | 96.2 |
|  |  |  |  | 15 | 4.6 | 96.0 |
|  |  |  |  | 30 | 4.8 | 97.1 |
|  |  |  |  | 60 | 5.1 | 94.2 |

The invention claimed is:

1. A process for isomerization of paraffin hydrocarbon feed in the presence of a composite catalyst containing (a) an ionic liquid catalyst comprised of a N-containing heterocyclic and/or aliphatic organic cation and an inorganic anion derived from metal halides or mixed metal halides, and (b) a metal salt additive selected from the group consisting of (i) at least one metal salt containing a cation of groups 6, 8, 11 or 12 metals, (ii) a mixed metal compound containing at least one cation chosen from group 6, 8, 11 or 12 metals, and (iii) an inorganic or organometallic co-ordination compound containing at least one metal chosen from group 6, 8, 11 or 12 as cationic, neutral or anionic complex.

2. A process of claim 1, wherein the cation of the ionic liquid catalyst is an N-aliphatic moiety with one or more alkyl or aryl groups.

3. A process of claim 2, wherein the N-aliphatic moiety is an ammonium compound and/or an alkyl substituted pyridinium, piperidinium or quinolinium compound.

4. A process of claim 1, wherein the anion of the ionic liquid is derived from a metal halide with strong Lewis acidic properties.

5. A process of claim 1, wherein the ionic liquid catalyst is obtained by combining N-containing heterocyclic and/or N-containing aliphatic organic compounds with one or more metal halides in a molar ratio of between 1:3 and 1:0.5.

6. A process of claim 1, wherein the metal halide is selected from $AlCl_4^-$, $AlBr_4^-$, $GaCl_4^-$, $Al_xCl_{2x+1}^-$, wherein $1<x<2$, and $Al_xCl_{2x}Br^-$, $1<x<2$.

7. A process of claim 1, where the metal cation of the salt additive is Mo(V), Fe(III) or Cu(II).

8. A process of claim 1, wherein the molar ratio between the metal part of the ionic liquid and the metal salt additive is above 1/1.

9. A process of claim 1, wherein the composite catalyst is pre-treated by heating between 0.5 h and 24 h at a temperature below 250° C. and/or ultrasound treatment between 0.5 h and 24 h.

10. A process of claim 1, wherein the conversion is performed at a pressure from 1 to 60 bar and a temperature from −30° C. to 150° C.

11. A process of claim 1, wherein the hydrocarbon feed: catalyst volume ratio is from 20:1 to 1:20.

* * * * *